United States Patent
Cho et al.

(10) Patent No.: US 12,070,487 B2
(45) Date of Patent: Aug. 27, 2024

(54) PHARMACEUTICAL COMPOSITION COMPRISING PIBF PROTEIN AS ACTIVE INGREDIENT FOR PREVENTION OR TREATMENT OF INFLAMMATORY DISEASE

(71) Applicants: UNIVERSITY OF ULSAN FOUNDATION FOR INDUSTRY COOPERATION, Ulsan (KR); THE ASAN FOUNDATION, Seoul (KR)

(72) Inventors: You Sook Cho, Seongnam-si (KR); Jun Pyo Choi, Seoul (KR); In Jeoung Baek, Seoul (KR); Hyouk Soo Kwon, Goyang-si (KR); So Young Park, Seoul (KR)

(73) Assignees: UNIVERSITY OF ULSAN FOUNDATION FOR INDUSTRY COOPERATION, Ulsan (KR); THE ASAN FOUNDATION, Seoul (KR)

( * ) Notice: Subject to any disclaimer, the term of this patent is extended or adjusted under 35 U.S.C. 154(b) by 566 days.

(21) Appl. No.: 17/418,684

(22) PCT Filed: Dec. 24, 2019

(86) PCT No.: PCT/KR2019/018394
§ 371 (c)(1),
(2) Date: Jun. 25, 2021

(87) PCT Pub. No.: WO2020/138912
PCT Pub. Date: Jul. 2, 2020

(65) Prior Publication Data
US 2022/0088125 A1  Mar. 24, 2022

(30) Foreign Application Priority Data
Dec. 28, 2018 (KR) .................. 10-2018-0172897

(51) Int. Cl.
*A61K 38/17* (2006.01)
*A61K 45/06* (2006.01)
*A61P 11/06* (2006.01)

(52) U.S. Cl.
CPC .......... *A61K 38/1709* (2013.01); *A61K 45/06* (2013.01); *A61P 11/06* (2018.01)

(58) Field of Classification Search
None
See application file for complete search history.

(56) References Cited

U.S. PATENT DOCUMENTS 10,231,976 B2  3/2019  Du
2004/0142394 A1  7/2004  Szekeres-Bartho et al.

FOREIGN PATENT DOCUMENTS

| JP | 2006-230407 A | 9/2006 | |
|---|---|---|---|
| JP | 5913136 B2 | 4/2016 | |
| WO | WO-03100428 A2 * | 12/2003 | ............. C07K 16/18 |
| WO | WO 2011/097571 A2 | 8/2011 | |

OTHER PUBLICATIONS

Amaral et al. ("Progesterone induced blocking factor improves fetal growth restriction possibly by reducing inflammation and placental cytolytic NK cells in response to placental ischemia during pregnancy," The FASEB Journal, 2018, vol. 32, p. 729.5) (Year: 2018).*
Korean Office Action issued May 10, 2021 in Korean Patent Application No. 10-2018-0172897 (submitting English translation only), 3 pages.
Korean Office Action issued Nov. 22, 2021 in Korean Patent Application No. 10-2018-0172897 (submitting English translation only), 4 pages.
Raquel Prudente de Carvalho Baldacaral, et al., "Association Between Asthma and Female Sex Hormones" The Sao Paulo Med. J., vol. 135, No. 1, 2017, pp. 4-14.
International Search Report issued on Apr. 14, 2020 in PCT/KR2019/018394 filed on Dec. 24, 2019, 3 pages.
Srivastava, M. D. et al., "Expression and modulation of progesterone induced blocking factor (PIBF) and innate immune. Factors in human leukemia cell lines by progesterone and mifepristone," Leukemia & Lymphoma, vol. 48, No. 8, 2007, pp. 1610-1617.
Sasha Tait, A. et al., "The role of glucocorticoids and progestins in inflammatory, autoimmune, and infectious disease," Journal of Leukocyte Biology, vol. 84, 2008, pp. 924-931.
Polgar, B. et al., "Molecular Cloning and Immunologic Characterization of a Novel cDNA Coding for Progesterone-Induced Blocking Factor," The Journal of Immunology, vol. 171, 2003, pp. 5956-5963, 10 total pages.
Szekeres-Bartho, J. et al., "PIBF: The Double Edged Sword. Pregnancy and Tumor," American Journal of Reproductive Immunology, vol. 64, 2010, pp. 77-86.

* cited by examiner

*Primary Examiner* — Christina Bradley
(74) *Attorney, Agent, or Firm* — Oblon, McClelland, Maier & Neustadt, L.L.P.

(57) ABSTRACT

The present invention relates to a pharmaceutical composition comprising a progesterone-induced blocking factor (PIBF) protein as an active ingredient for prevention or treatment of inflammatory disease. In the present invention, menopausal asthma animal models have been experimentally identified to decrease airway inflammation when treated with PIBF protein. Thus, the composition can be advantageously used in postmenopausal female asthma patients.

4 Claims, 18 Drawing Sheets
Specification includes a Sequence Listing.

FIG. 8A

GGCCACAGCGGCCGATGTCCACTCGATGTCTCGAAAAATTTCAAAGGAGTCAA
AAAAAGTGAACATCTCTAGTTCTCTGGAATCTGAAGATATTAGTTTAGAAACAA
CAGTTCCTACGGATGATATTTCCTCATCAGAAGAGCGAGAGGGCAAAGTCAGA
ATCACCAGGCAGCTAATTGAACGAAAAGAACTACTTCATAATATTCAGTTACTA
AAAATTGAGCTATCCCAGAAAACTATGATGATCGACAATTTGAAAGTGGATTAT
CTTACAAAGATTGAAGAATTGGAGGAGAAACTTAATGATGCACTTCACCAGAAG
CAGCTACTAACATTGAGATTAGACAACCAATTGGCTTTTCAACAGAAAGATGCC
AGCAAATATCAAGAATTAATGAAACAAGAAATGGAAACCATTTTGTTGAGACAG
AAACAACTAGAAGAGACAAATCTTCAGCTAAGAGAAAAGCTGGAGATGTTCG
TCGAAACCTGCGTGACTTTGAGTTGACAGAAGAGCAATATATTAAATTAAAAGC
TTTTCCTGAAGATCAGCTTTCTATTCCTGAATATGTATCTGTTCGCTTCTATGAGC
TAGTGAATCCATTAAGAAAGGAAATCTGTGAACTACAAGTGAAAAGAATATCC
TAGCAGAAGAATTAAGTACAAACAAAAACCAACTGAAGCAGCTGACAGAGGAA
TTGGCAGCAATGAAACAGATTCTCGTTAAGATGCATAGTAAACATTCTGAGAAC
AGCTTACTTCTCACTAAAACAGAACCAAAACATGTGACAGAAAATCAGAAATCA
AAGACTTTGAATGTGCCTAAAGAGCATGAAGACAATATATTTACACCTAAACCA
ACACTCTTTACTAAAAAGAAGCACCTGAGTGGTCTAAGAAACAAAAGATGAA
GACCTTGGCCGCGTCGGCC     GAGCCCAAATCTTGTGACAAAACTCACA  Nhel
CATGCCCACCGTGCCCAGCACCTGAACTCCTGGGGGGACCGTCAGTCTTCCTCT
TCCCCCCAAAACCCAAGGACACCCTCATGATCTCCCGGACCCCTGAGGTCACAT
GCGTGGTGGTGGACGTGAGCCACGAAGACCCTGAGGTCAAGTTCAACTGGTAC
GTGGACGGCGTGGAGGTGCATAATGCCAAGACAAAGCCGCGGGAGGAGCAGT
ACAACAGCACGTACCGTGTGGTCAGCGTCCTCACCGTCCTGCACCAGGACTGG
CTGAATGGCAAGGAGTACAAGTGCAAGGTCTCCAACAAAGCCCTCCCAGCCCC
CATCGAGAAAACCATCTCCAAAGCCAAAGGGCAGCCCCGAGAACCACAGGTGT
ACACCCTGCCCCCATCCCGGGATGAGCTGACCAAGAACCAGGTCAGCCTGACC
TGCCTGGTCAAAGGCTTCTATCCCAGCGACATCGCCGTGGAGTGGGAGAGCAA
TGGGCAGCCGGAGAACAACTACAAGACCACGCCTCCCGTGCTGGACTCCGACG
GCTCCTTCTTCCTCTACAGCAAGCTCACCGTGGACAAGAGCAGGTGGCAGCAG
GGGAACGTCTTCTCATGCTCCGTGATGCATGAGGCTCTGCACAACCACTACACG
CAGAAGAGCCTCTCCCTGTCTCCGGGTAAATGATAGCTCGAG

FIG 8B

MSRKISKESKKVNISSSLESEDISLETTVPTDDISSSEEREGKVRITRQ
LIERKELLHNIQLLKIELSQKTMMIDNLKVDYLTKIEELEEKLNDALHQKQLLTLRLD
NQLAFQQKDASKYQELMKQEMETILLRQKQLEETNLQLREKAGDVRRNLRDFELT
EEQYIKLKAFPEDQLSIPEYVSVRFYELVNPLRKEICELQVKKNILAEELSTNKNQLKQ
LTEELAAMKQILVKMHSKHSENSLLLTKTEPKHVTENQKSKTLNVPKEHEDNIFTPK
PTLFTKKEAPEWSKKQKMKTLAASA EPKSCDKTHTCPPCPAPELLGGPSVFLFP
PKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSFFLYSKL
TVDKSRWQQGNVFSCSVMHEALHNHYTQKSLSLSPGK

PHARMACEUTICAL COMPOSITION COMPRISING PIBF PROTEIN AS ACTIVE INGREDIENT FOR PREVENTION OR TREATMENT OF INFLAMMATORY DISEASE

CROSS-REFERENCE TO RELATED APPLICATIONS

This application is a 371 of PCT/KR2019/018394, filed on Dec. 24, 2019, which claims the benefit of priority from Korean Patent Application No. 10-2018-0172897, filed on Dec. 28, 2018, the contents of each of which are incorporated herein by reference in their entirety.

REFERENCE TO SEQUENCE LISTING

In accordance with 37 CFR § 1.52(e)(5) and with 37 CFR § 1.831, the specification makes reference to a Sequence Listing submitted electronically as a .txt file named "537614US_ST25.txt". The .txt file was generated on Aug. 23, 2021 and is 22,905 bytes in size. The entire contents of the Sequence Listing are hereby incorporated by reference.

TECHNICAL FIELD

The present invention relates to a pharmaceutical composition for preventing or treating an inflammatory disease, which includes a progesterone-induced blocking factor (PIBF) protein as an active ingredient.

BACKGROUND ART

Asthma is a relatively common chronic disease causing chronic inflammation and obstruction of the airways, with a prevalence of approximately 5% in Korea. Chronic obstructive airway disease is a disease whose prevalence and mortality are rapidly increasing, and falls within "a group of diseases requiring special attention," which is included in the four groups of non-infectious diseases recently designated by the WHO.

Asthma is a disease that is known to have various disease severities and prognoses, as well as prevalence rates, depending on race, gender, age, and region. However, the prevalence of asthma tends to increase throughout the world, and the burden of disease is increasing accordingly. In particular, asthma has a consistently high level of prevalence in women, and is also increasing in a socially vulnerable class such as the elderly populations. Among these, the prevalence of asthma is rapidly increasing by 10% or more in postmenopausal elderly women, and an increase in onset of asthma and the expression of severe symptoms are observed, but their cause has yet to be determined.

Especially in elderly women, high proportion of patients with severe asthma is observed characterized by poor symptom control, persistent asthma exacerbations, and progressive lung function decline despite treatment with high-dose inhaled corticosteroids. In the Western countries having high asthma incidence, the proportion of severe asthma patient constitutes approximately 10% of the all asthma patients, and also accounts for 5 to 10% in Korea and Japan. Severe asthma constitutes approximately 5 to 10% of all asthma cases, but the medical expenditures spent to treat severe asthma constitute 60% or more of the total medical expenditures associated with asthma.

At present, severe asthma has no definite treatment, and causes enormous trouble in daily life. In particular, elderly women have a high risk of side effects due to the use of steroids. When systemic or inhaled steroids are used for a long time, the incidence of fractures by osteoporosis, depression, insomnia, obesity, diabetes, coronary artery disease, and iatrogenic Cushing syndrome is known to increase, and the social costs caused by these side effects are also problematic.

A difference of clinical features such as asthma prevalence and disease severity according to gender has been observed in various epidemiological investigations, and the hypothesis that an effect of female hormones is involved in the pathogenesis of the disease is gaining momentum. However, treating certain disease through control of female hormones has never been proven so far. Moreover, long-term administration of female hormones after menopause raises the risk of serious side effects such as cancer and thrombosis, which makes it hard to be used to treat lifelong chronic disease.

PRIOR ART DOCUMENT

Patent Document: JP 5913136 B2

DISCLOSURE

Technical Problem

To solve the related-art problems, it is an object of the present invention to provide a pharmaceutical composition for preventing or treating an inflammatory disease, which includes a progesterone-induced blocking factor (PIBF) protein as an active ingredient.

It is another aspect of the present invention to provide a food composition for preventing or ameliorating an inflammatory disease, which includes a progesterone-induced blocking factor (PIBF) protein as an active ingredient.

However, the technical objects of the present invention are not limited thereto, and other objects of the present invention which are not stated herein will become more apparent to those of ordinary skill in the art by describing in detail exemplary embodiments thereof.

Technical Solution

One aspect of the present invention provides a pharmaceutical composition for preventing or treating an inflammatory disease, which includes a progesterone-induced blocking factor (PIBF) protein as an active ingredient.

The term "prevention" refers to a decrease in the occurrence of pathological cells or a decrease in degree of damage and loss of cells in an animal. The prevention may be complete or partial. In this case, the prevention may refer to a situation in which the occurrence of pathological cells or the cell death or loss of nerve cells in a subject decreases compared to when the composition for preventing or treating an inflammatory disease is not used.

Also, the term "treatment" refers to all types of actions for clinical intervention intended to alter a target to be treated or a natural process of cells. In this case, the treatment may be performed while a clinically pathological condition progresses or performed to prevent the progression of the clinically pathological condition. Desired therapeutic effects may include preventing the occurrence or recurrence of diseases, alleviating symptoms, reducing all direct or indirect pathological outcomes of diseases, preventing metastasis, delaying disease progression, improving or alleviating conditions, and improving prognoses. That is, the treatment may be interpreted to encompass all types of actions intended to improve or completely cure the symptoms of an inflammatory disease using the pharmaceutical composition, but the present invention is not particularly limited thereto.

The composition may be used to prevent or treat an inflammatory disease in postmenopausal women.

The PIBF protein may be applied in the form of a recombinant protein in which FC is bound to PIBF in order to optimize a drug by extending a half-life of the drug and stabilizing the drug. Here, the recombinant protein may consist of a polypeptide encoded by a base sequence set forth in SEQ ID NO: 1 or a base sequence having a homology to SEQ ID NO: 1, preferably a homology of 75% or more, more preferably 85% or more, further preferably 90% or more, and most preferably 95% or more to SEQ ID NO: 1, or an amino acid set forth in SEQ ID NO: 2 or an amino acid sequence having a homology to SEQ ID NO: 2, preferably a homology of 75% or more, more preferably 85% or more, further preferably 90% or more, and most preferably 95% or more to SEQ ID NO: 2.

Also, the recombinant protein as described above may be recombined with albumin, an albumin binding protein, IgG as well as FC, and may also be recombined by PEGylation, and the like.

The PIBF protein may have a molecular weight of 25 to 45 kDa, preferably a molecular weight of 30 to 40 kDa. More preferably the PIBF protein may have a molecular weight of 35 kDa.

The inflammatory disease may include asthma, autoimmune diseases, chronic inflammation, chronic prostatitis, glomerulonephritis, hypersensitivity, inflammatory bowel disease, pelvic inflammatory diseases, rheumatoid arthritis, celiac disease, sarcoidosis, interstitial cystitis, or vasculitis.

The composition may further include one or more drugs selected from the group consisting of an antiinflammatory agent, a bronchodilator, an antihistamine, a decongestant, and an antitussive. For example, the composition may further include an A2A agonist, an A2B antagonist, an antihistamine, a beta-2 adrenergic receptor agonist, a caspase inhibitor, an LTB4 antagonist, an LTD4 antagonist, a PDE4 inhibitor, a mucolytic agent, a matrix metalloproteinase inhibitor (MMPi), a leukotriene, an antibiotic, an anti-neoplastic, a peptide, a vaccine, an elastase inhibitor, sodium cromoglycate, or the like. Such compounds may be further included as an agent for reinforcing the therapeutic activity of the PIBF protein or as a means for reducing a desired dose of the PIBF protein or lessening potential side effects of the PIBF protein.

The pharmaceutical composition may be formulated into the form of an oral formulation, a preparation for external use, a suppository, or a sterile injectable solution. The oral formulation may be in the form of a powder, a granule, a tablet, a capsule, a suspension, an emulsion, a syrup, an inhalant, an aerosol, or the like. In this case, the formulations may be prepared by conventional methods.

When the composition is formulated, the composition may be used together with a diluent, a carrier, an excipient, or the like.

The carrier, excipient, or diluent that may be used in the present invention includes lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, mineral oil, or the like.

A solid preparation for oral administration includes a tablet, a pill, a powder, a granule, a capsule, and the like. Such a solid preparation may be prepared by mixing the compound with at least one or more excipients, for example starch, calcium carbonate, sucrose or lactose, gelatin, or the like.

Also, lubricants such as magnesium stearate, talc, and the like may also be used in addition to the simple excipients. A liquid preparation for oral administration includes a suspending agent, an oral liquid, an emulsifying agent, a syrup, and the like. In this case, such a liquid preparation may include various excipients, for example a wetting agent, a sweetening agent, a flavoring agent, a preservative, and the like in addition to the commonly used simple diluents such as water, liquid paraffin, and the like.

A preparation for parenteral administration may include a sterilized aqueous solution, a non-aqueous solvent, a suspending agent, an emulsifying agent, a lyophilized preparation, and a suppository. Vegetable oils such as propylene glycol, polyethylene glycol, olive oil, and the like, injectable esters such as ethyl oleate, and the like may be used as the non-aqueous solvent and the suspending agent. Witepsol, Macrogol, Tween 61, cacao butter, laurin butter, glycerinated gelatin, and the like may be used as a base for the suppository.

An effective amount of the progesterone-induced blocking factor (PIBF) protein as the active ingredient of the pharmaceutical composition for preventing or/and treating an inflammatory disease may vary depending on a route of administration, the age and sex of a patient, and the severity of a disease. In general, the PIBF protein may be administered once or several times a day at a dose of 10 to 1,000 µg/kg.

The pharmaceutical composition according to the present invention may be administered into a mammal such a rat, a mouse, livestock, a human, and the like through various routes of administration. The administration may be performed by conventional methods. For example, the pharmaceutical composition may be administered orally, rectally, intravenously, intramuscularly, subcutaneously, or by intrabronchial inhalation.

Also, the present invention provides a food composition for preventing or ameliorating an inflammatory disease, which includes a progesterone-induced blocking factor (PIBF) protein as the active ingredient.

The food composition according to the present invention may be prepared in various forms using conventional methods known in the art. General foods may be prepared by adding the PIBF of the present invention to drinks (including alcoholic drinks), fruits and processed foods thereof (e.g., canned fruits, bottled foods, jam, marmalade juices, and the like), fish, meats and processed foods thereof (e.g., ham, sausage, corned beef, and the like), bread and noodles (e.g., udon, buckwheat noodles, ramen, spaghetti, macaroni, and the like), fruit juices, various drinks, cookies, taffy, dairy products (e.g., butter, cheese, and the like), edible vegetable fats and oils, margarine, vegetable proteins, retort foods, frozen foods, various condiments (e.g., fermented soybean paste, soy sauce, other sauces, and the like), and the like, but the present invention is not limited thereto. Also, a nutritional supplement may be prepared by adding the PIBF protein of the present invention to capsules, tablets, pills, and the like, but the present invention is not limited thereto. In addition, the PIBF protein of the present invention itself may be liquefied, granulized, encapsulated, and pulverized so that it can be prepared in the form of teas, juices, and drinks for consumption. Further, the PIBF protein of the present invention may be prepared in the form of a powder or a concentrate so that the PIBF protein of the present invention can be used in the form of a food additive. The PIBF protein according to the present invention may be included at 0.01 to 50% by weight, based on the total weight of the entire composition, but the present invention is not limited thereto.

The food composition may contain various nutrients, vitamins, electrolytes, a flavoring agent, a coloring agent, pectic acid or a salt thereof, alginic acid or a salt thereof, organic acids, a protective colloidal thickening agent, a pH controller, a stabilizing agent, a preservative, glycerin, an alcohol, a carbonating agent, or the like. The proportions of such additives are not very important, but are generally selected from a range of 0.01 to 0.1 parts by weight based on 100 parts by weight of the composition of the present invention.

Also, the present invention provides a method of preventing or treating an inflammatory disease, which includes administering or dosing the composition including a progesterone-induced blocking factor (PIBF) protein as the active ingredient to a subject.

Further, the present invention provides a use of the composition including a progesterone-induced blocking factor (PIBF) protein as the active ingredient for preventing or treating an inflammatory disease.

Advantageous Effects

The present invention can provide a pharmaceutical composition for preventing or treating an inflammatory disease, which includes a progesterone-induced blocking factor (PIBF) protein as an active ingredient. In particular, in the present invention, an animal model of postmenopausal asthma has been experimentally confirmed to have decreased airway inflammation when treated with the PIBF protein. Thus, the composition can be usefully used in postmenopausal female asthma patients.

DESCRIPTION OF DRAWINGS

FIG. 8A depicts the polynucleotide sequence of a recombinant DNA construct described by SEQ ID NO: 1. The polynucleotide sequences of the sfiI (GGCCACAGCGGC, SEQ ID NO: 6), NheI (TTGGCCGCGTCGGCC, SEQ ID NO: 7) and XhoI (CTCGAG) restriction sites are also depicted. The two stop codons TGATAG are shown at the end of SEQ ID NO: 1 upstream from the XhoI site. SEQ ID NO: 4 corresponds to nucleotides 26 to 919 of SEQ ID NO: 1. This DNA construct encodes PIBF1+FC.

FIG. 8B depicts the amino acid sequence of SEQ ID NO: 2 which is encoded by the coding sequence of SEQ ID NO: 1.

BEST MODE

Hereinafter, the present invention will be described in further detail with reference to embodiments thereof. These and other objects, features and advantages of the present invention will be readily understood with reference to the following embodiments. Therefore, it should be understood that the present invention may be embodied in various forms, but is not intended to limit the embodiments disclosed herein. In this case, the embodiments disclosed herein are provided to sufficiently convey the spirit of the present invention to those skilled in the art to which the present invention pertains. Therefore, it will be apparent that the following embodiments are not intended to limit the present invention.

According to the present invention, an anti-asthmatic inflammation effect of a 35 kDa PIBF protein has been confirmed in a female asthma mouse model in which menopause was induced through the following Examples. To date, focus has been mainly made on the pattern of inflammatory cells in the study on an asthma mechanism, or made on the study of the role of the inflammatory cells, and action mechanisms of several inflammatory cytokines. Based on the clinical diversity of asthma, the development of customized therapeutic agents according to clinical subtypes of asthma was recently proposed as an ideal direction for treatment of asthma. Asthma developing in elderly women after menopause is a unique clinical subtype, and thus elderly women urgently require customized treatment for this subtype. In this case, the present invention may be the most suitable technique. Also, the greatest advantage of the present invention is to avoid the use of steroids having a high risk of side effects in elderly female asthma patients.

EXAMPLES

Figure 1:
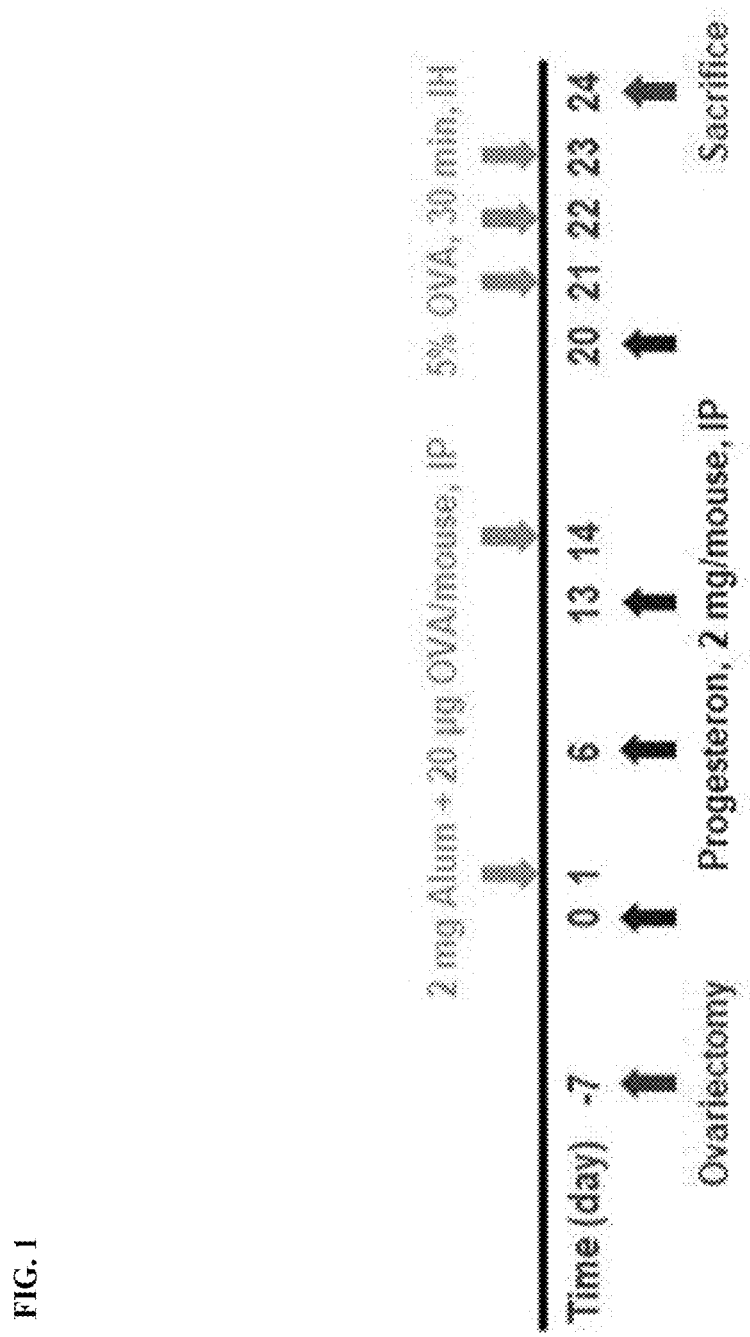
FIG. 1 is a schematic diagram showing an animal model protocol for identifying the relationship between female hormones and clinical types of asthma.
Figure 2A:
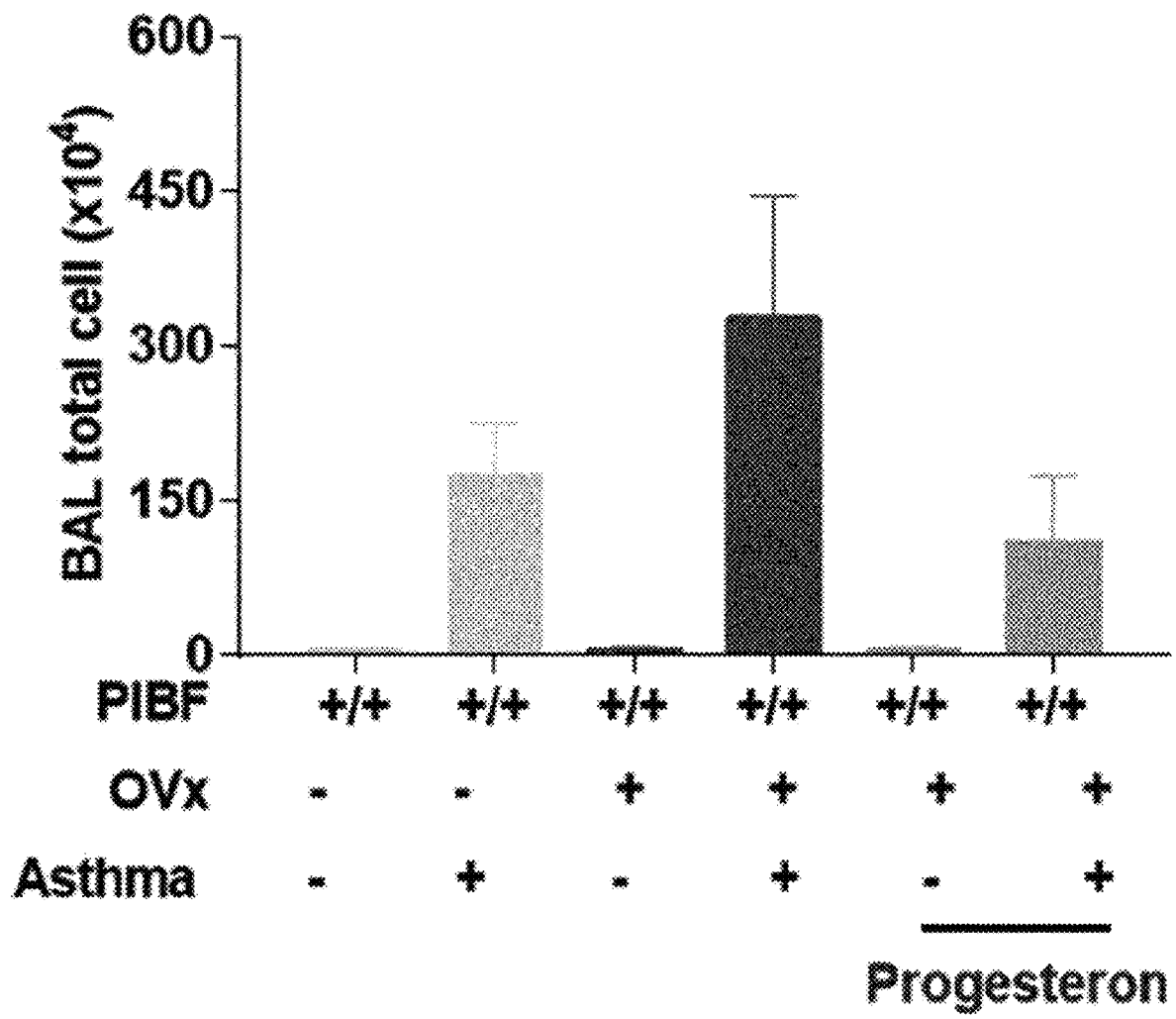
FIG. 2 shows the results of analyzing inflammatory cells in a bronchoalveolar lavage fluid in an animal model of postmenopausal female asthma.
Figure 2B:
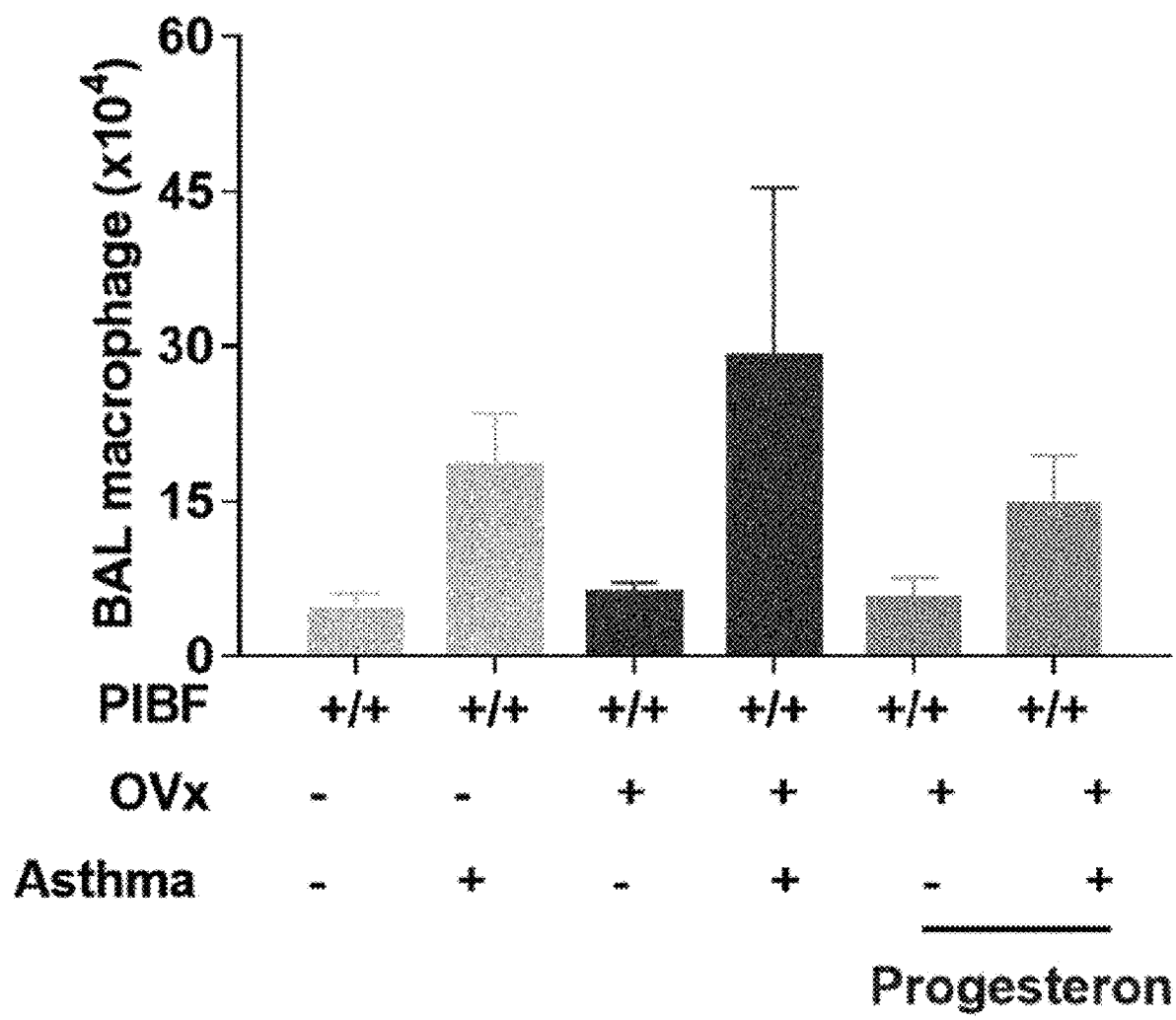
Figure 2C:
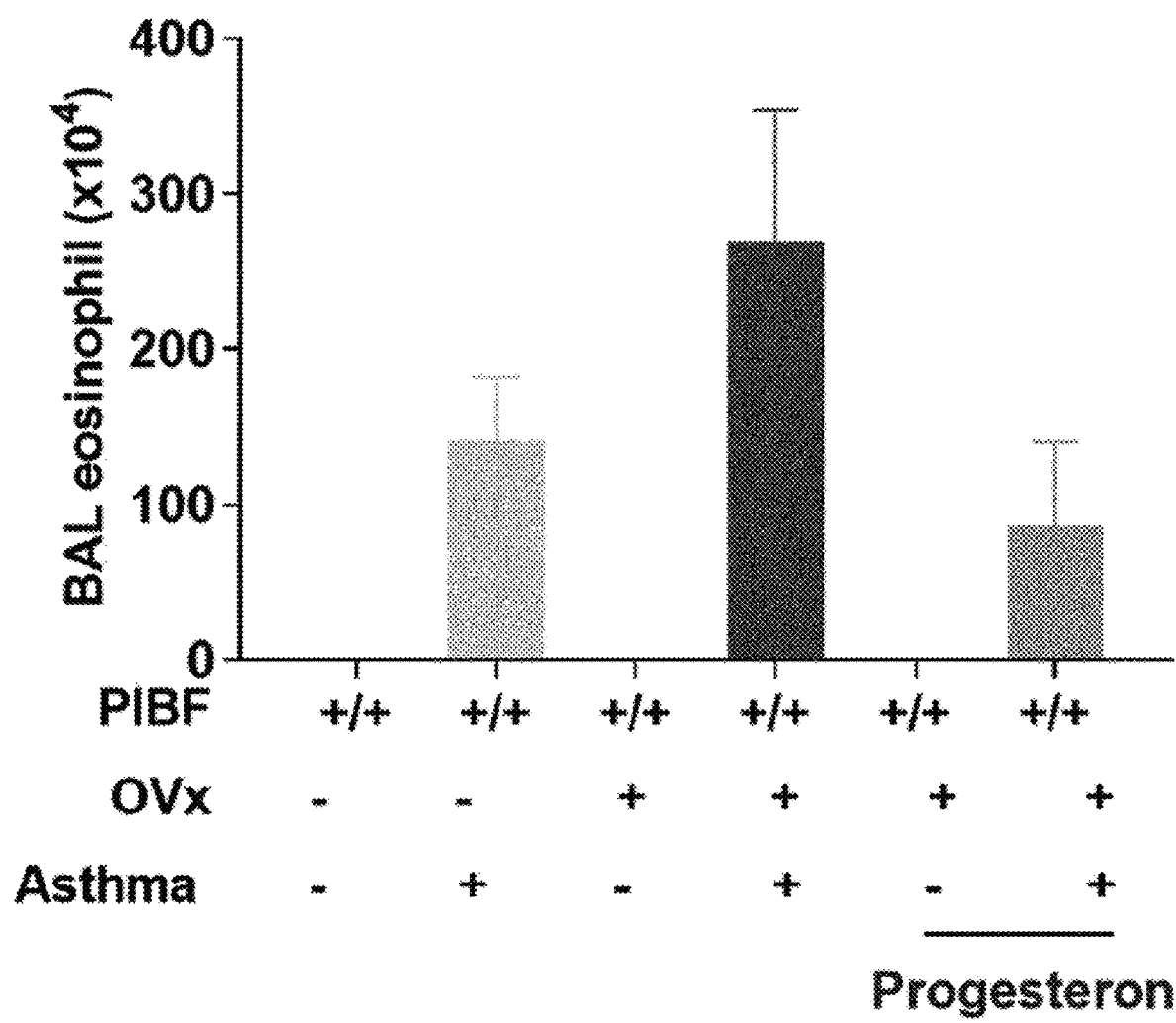
Figure 2D:
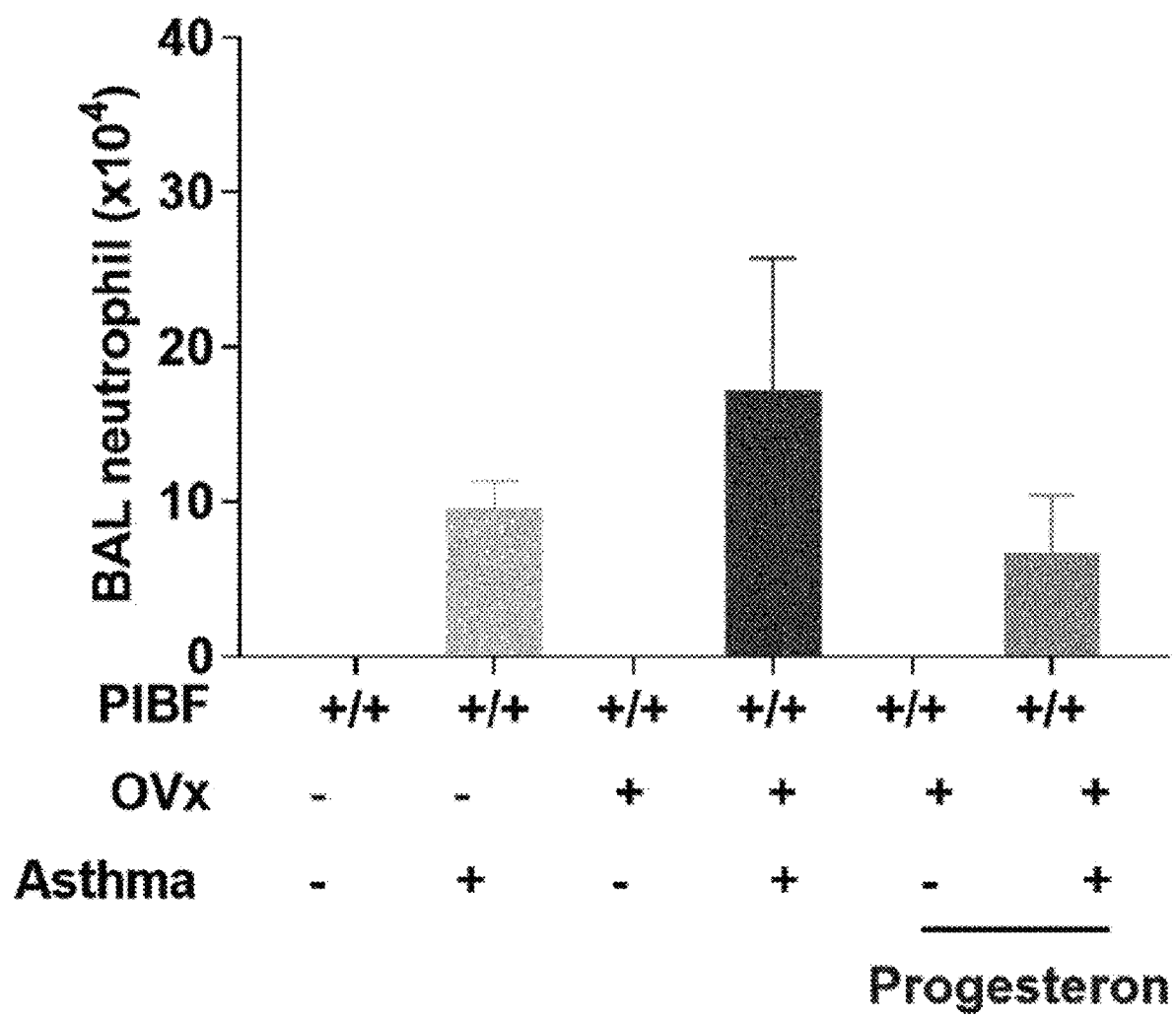
Figure 2E:
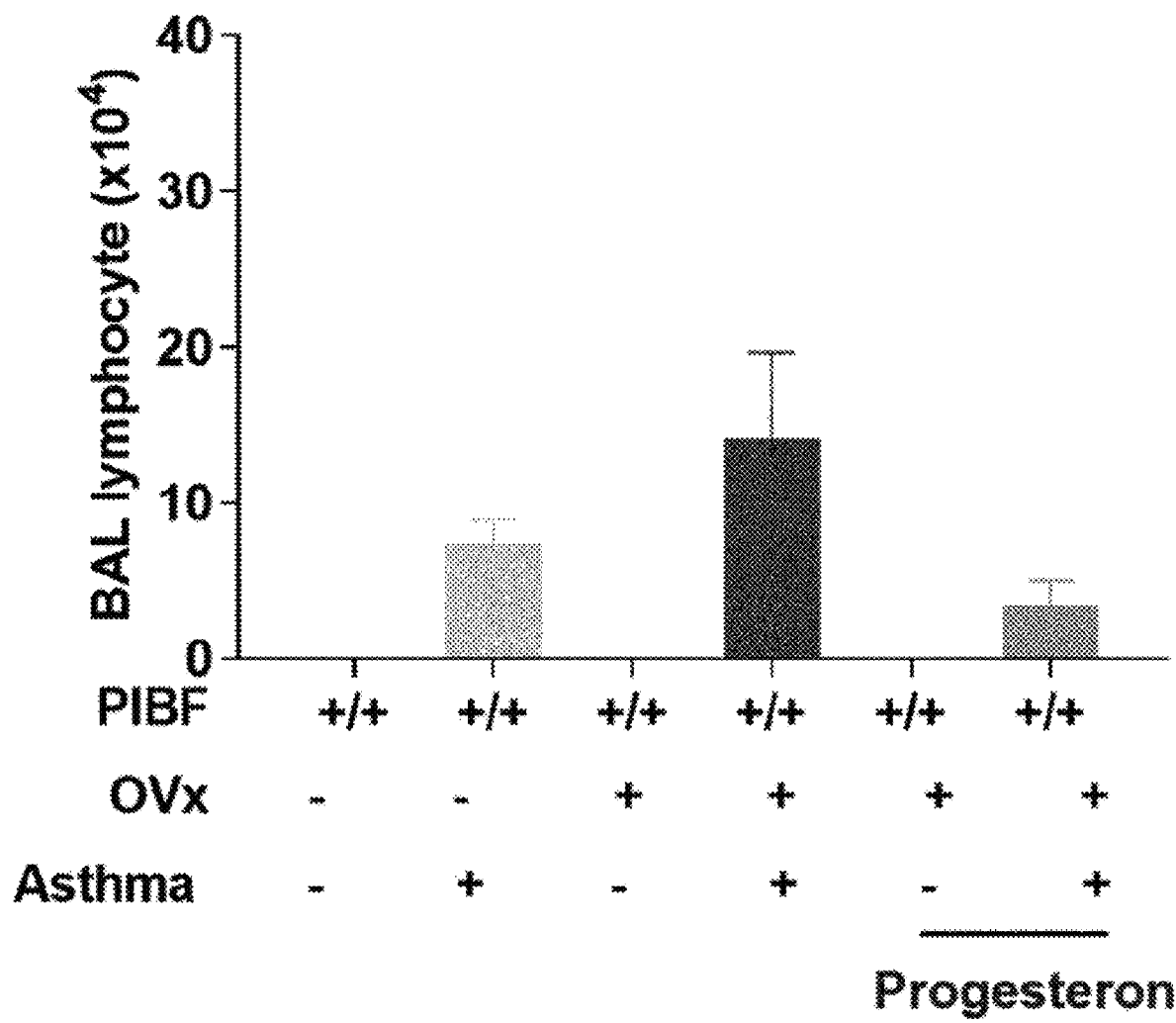

1. Experimental Methods 1-1: Analysis of Inflammatory Cells and Lung Tissues in Bronchoalveolar Lavage Fluid in Postmenopausal Female Asthma Animal Model To establish an animal model reflecting postmenopausal female asthma, 6-week-old female C57BL/6 mice (ORIENT BIO Inc.) were subjected to ovariectomy to induce menopause. After stabilization, an acute allergic asthma animal model was induced. To determine an effect of a female hormone on the clinical type of allergic asthma in this model, a female hormone was periodically injected as shown in the protocol of FIG. 1 to compare and evaluate the effects of the female hormone. On day 24 of establishment of the model, the mice were peritoneally anesthetized and thoracically incised. Thereafter, blood was collected from the heart using a 26 gauge syringe so that blood samples were taken simultaneously with euthanasia. Then, a catheter was inserted into the airway, and a bronchoalveolar lavage fluid (BALF) was obtained using 2 mL PBS and a syringe.

Next, after reperfusion with physiological saline, lung tissue was obtained. In this case, left lung was fixed in 10% formalin to perform a histopathological test, and the remainder was set aside for extraction of proteins and RNA and stored at −80° C. The total number of cells in the BALF was calculated using a hemocytometer. The cells were immediately cytospun, stained with Diff-Quik, and then differentially counted. The lung tissue was fixed for a day, embedded in paraffin melted at a temperature of 61° C. or less, and then cut into slides having a thickness of 4 μm using a sliding microtome. The observation of inflammation in the lung tissue was confirmed through H&E staining. An acute asthma animal model was induced as follows. On days 0 and 14, 20 μg of ovalbumin and 2 mg of alum were mixed with PBS to prepare 100 μL of the mixture. The mixture was intraperitoneally administered to induce systemic sensitization to OVA. On days 21, 22, and 23, 5% OVA was inhaled into the airway using a nebulizer to establish an animal model.

1-2: Analysis of Effect of Airway Inflammation in Asthma Model Using PIBF Gene Half-Deficient Transgenic Mice To confirm an effect of PIBF induced by the female hormone on a phenotype of asthma, a postmenopausal female asthma animal model was induced, and normal mice and PIBF half-deficient mice were treated with the female hormone. Thereafter, the influx of cells into a bronchoalveolar lavage fluid was analyzed. This experiment was performed in the same manner as in Example 1-1, except that the PIBF half-deficient mice were used.

Figure 6:
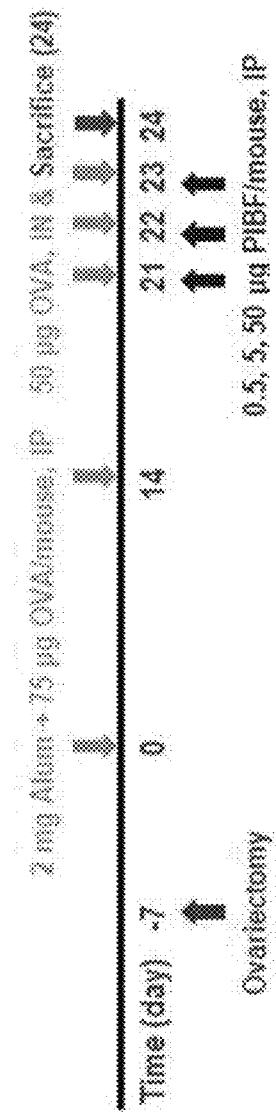
FIG. 6 is a schematic diagram showing a protocol for determining an effect of PIBF in an asthma animal model.
Figure 8C:
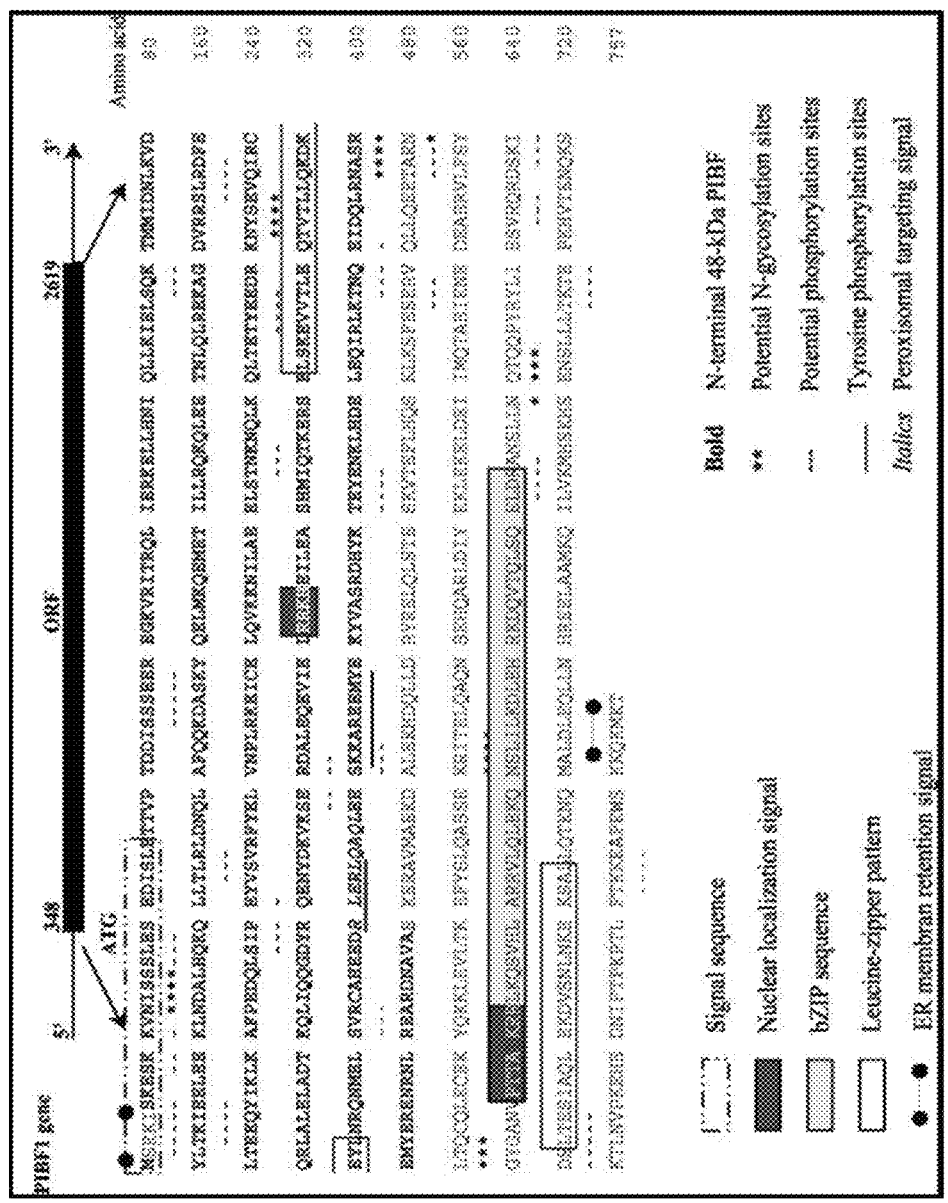
FIG. 8C depicts the amino acid sequence of SEQ ID NO: 3.

1-3: Analysis Results of Inflammatory Cell Influx in Bronchoalveolar Lavage Fluid and Lung Tissue Through PIBF Treatment An acute asthma animal model was established in the normal mice and the mice in which menopause was induced by ovariectomy, and treated with PIBF (a 35 kDa PIBF1 recombinant protein: SEQ ID NO: 1) as shown in the protocol of FIG. 6 to determine an effect of the PIBF. This experiment was performed in the same manner as in Example 1-1, except that the mice were treated with PIBF as shown in the protocol of FIG. 6. The PIBF recombinant protein has a form in which FC is bound to PIBF and was prepared by commissioning Y-Biologics Inc. The prepared recombinant protein had a polypeptide sequence encoded by the base sequence set forth in SEQ ID NO: 1 (FIG. 8A, PIBF1+FC) or an amino acid sequence set forth in SEQ ID NO: 2 (FIGS. 8A and 8B, PIBF1+FC).

2. Experimental Results 2-1: Results of Analysis of Inflammatory Cells and Lung Tissues in Bronchoalveolar Lavage Fluid in Postmenopausal Female Asthma Animal Model In the mice in which asthma was induced after the induction of menopause, the infiltration of inflammatory cells in the airway tended to increase compared to the normal mice. In this case, it was confirmed that the airway inflammation decreased again in the group treated with the female hormone (FIG. 2).

Figure 3:
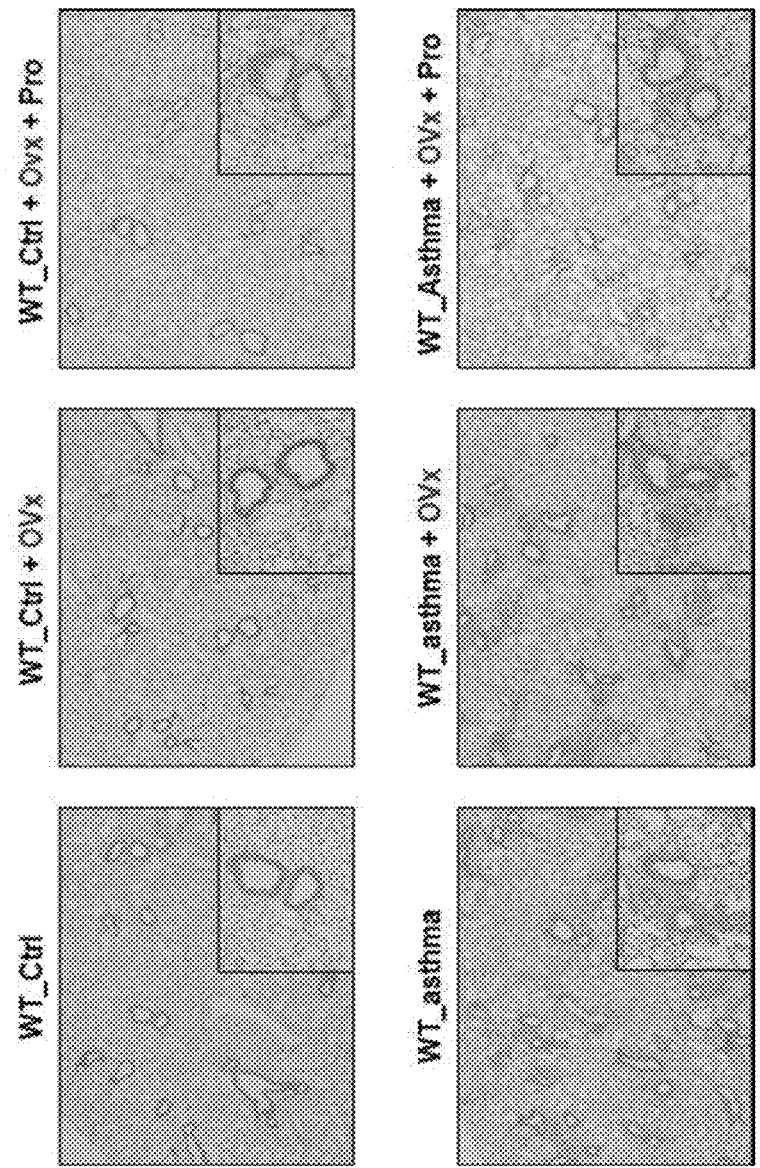
FIG. 3 shows the results of comparing levels of inflammation in lung tissue and changes in tissues in asthma model mice.
Figure 4A:
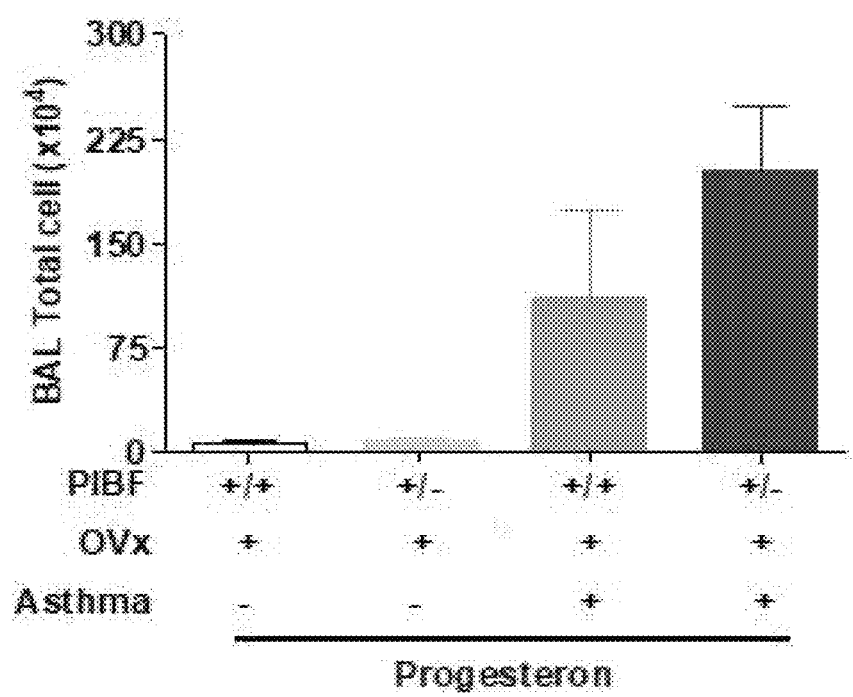
FIG. 4 shows the results of analyzing an effect of airway inflammation in an asthma model using PIBF gene half-deficient transgenic mice.
Figure 4B:
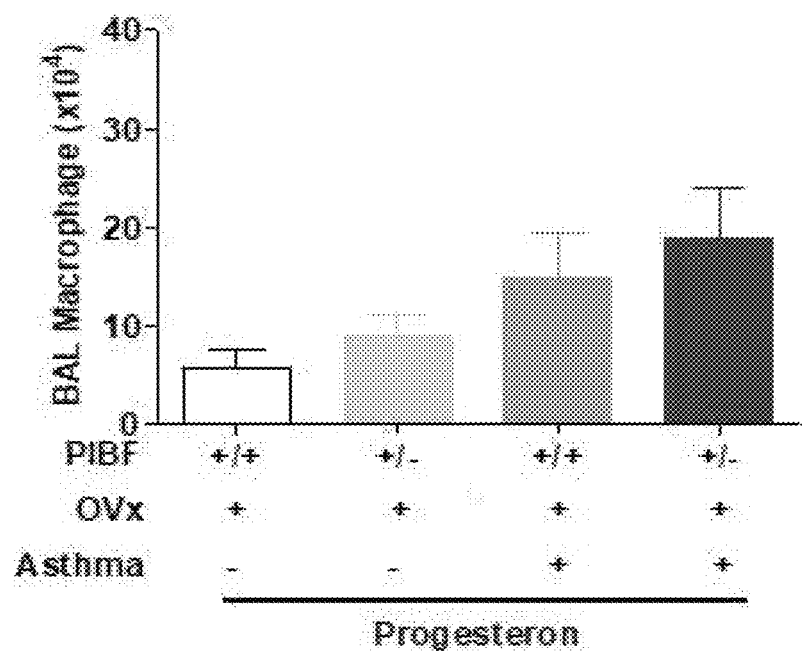
Figure 4C:
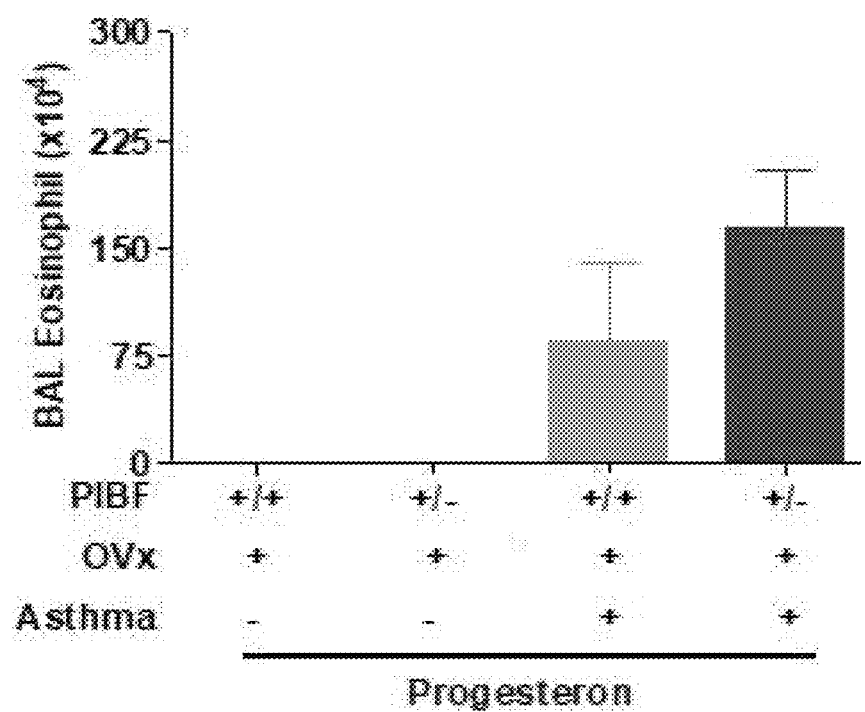
Figure 4D:
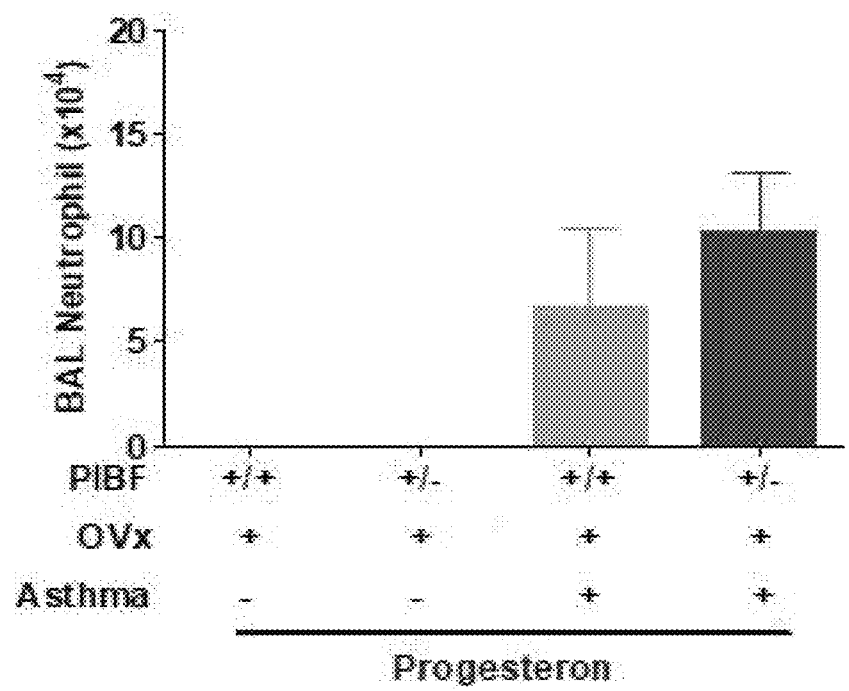
Figure 4E:
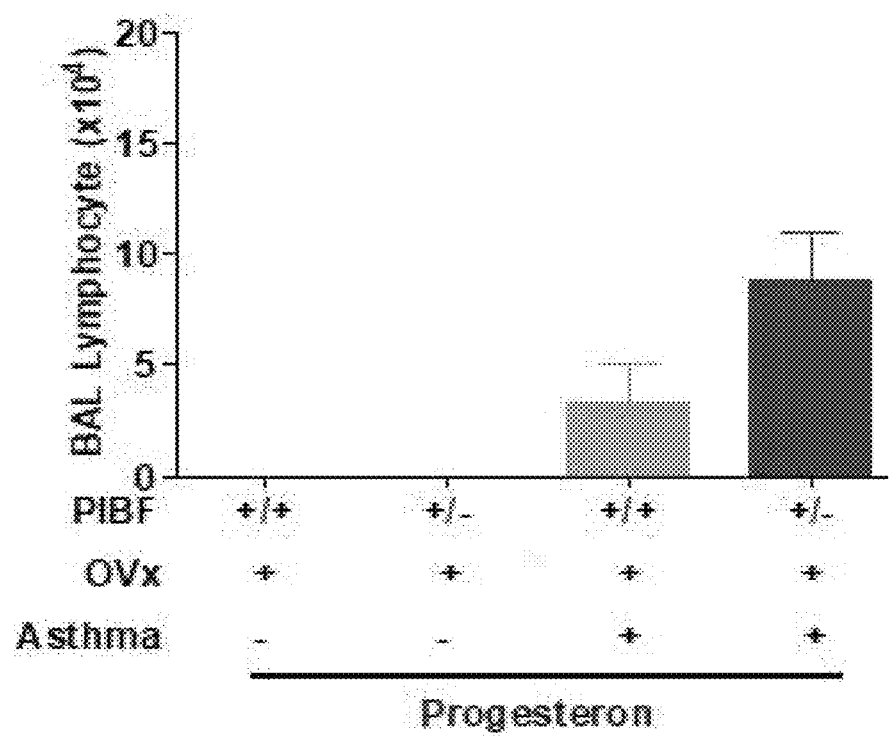

From the results of histological analysis, it was confirmed that the infiltration of inflammatory cells in the lung tissue increased in the mice having undergone the ovariectomy, compared to the normal mice, and then decreased when the mice were again treated with the female hormone (FIG. 3).

Figure 5:
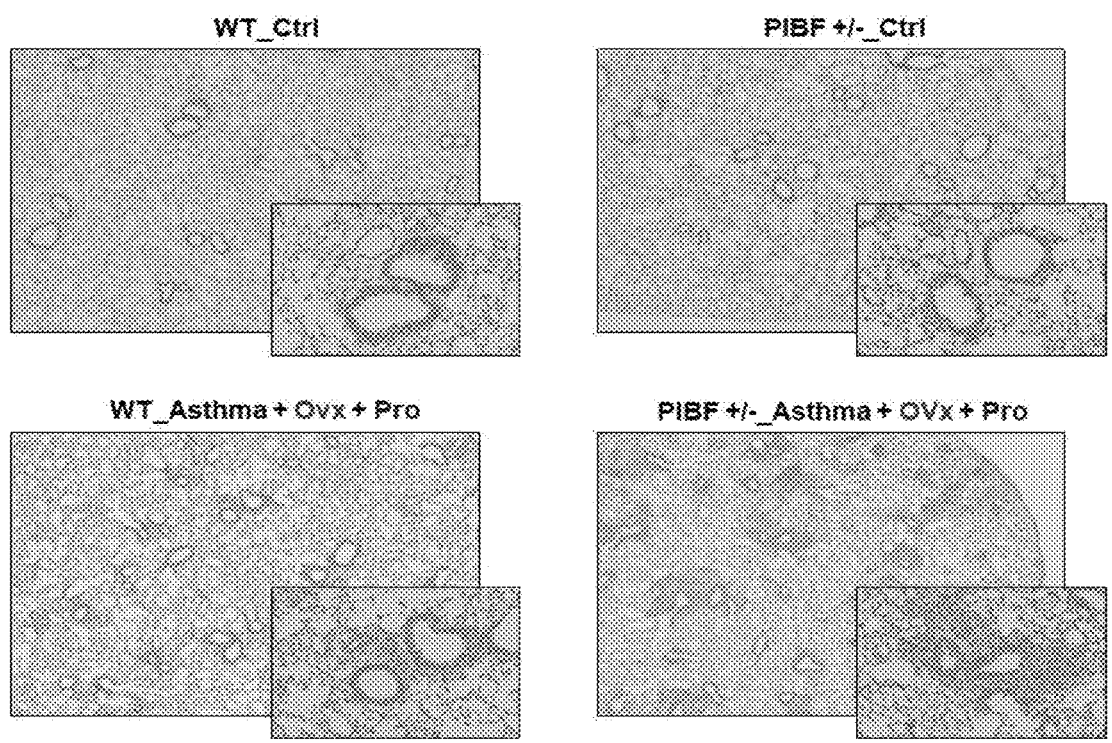
FIG. 5 shows the results of comparing levels of inflammation in lung tissue and changes in tissues in the PIBF gene half-deficient transgenic mice.

2-2: Effect of Airway Inflammation in Asthma Model Using PIBF Gene Half-Deficient Transgenic Mice As shown in FIG. 4, it was confirmed that the influx of inflammatory cells increased in the PIBF half-deficient mice. From the results of lung tissue analysis, in the mice in which asthma was induced among the PIBF half-deficient mice, it was also confirmed that the airway wall became thicker even when the mice were treated with the female hormone, and the infiltration of inflammatory cells increased, compared to the normal mice (FIG. 5).

Figure 7:
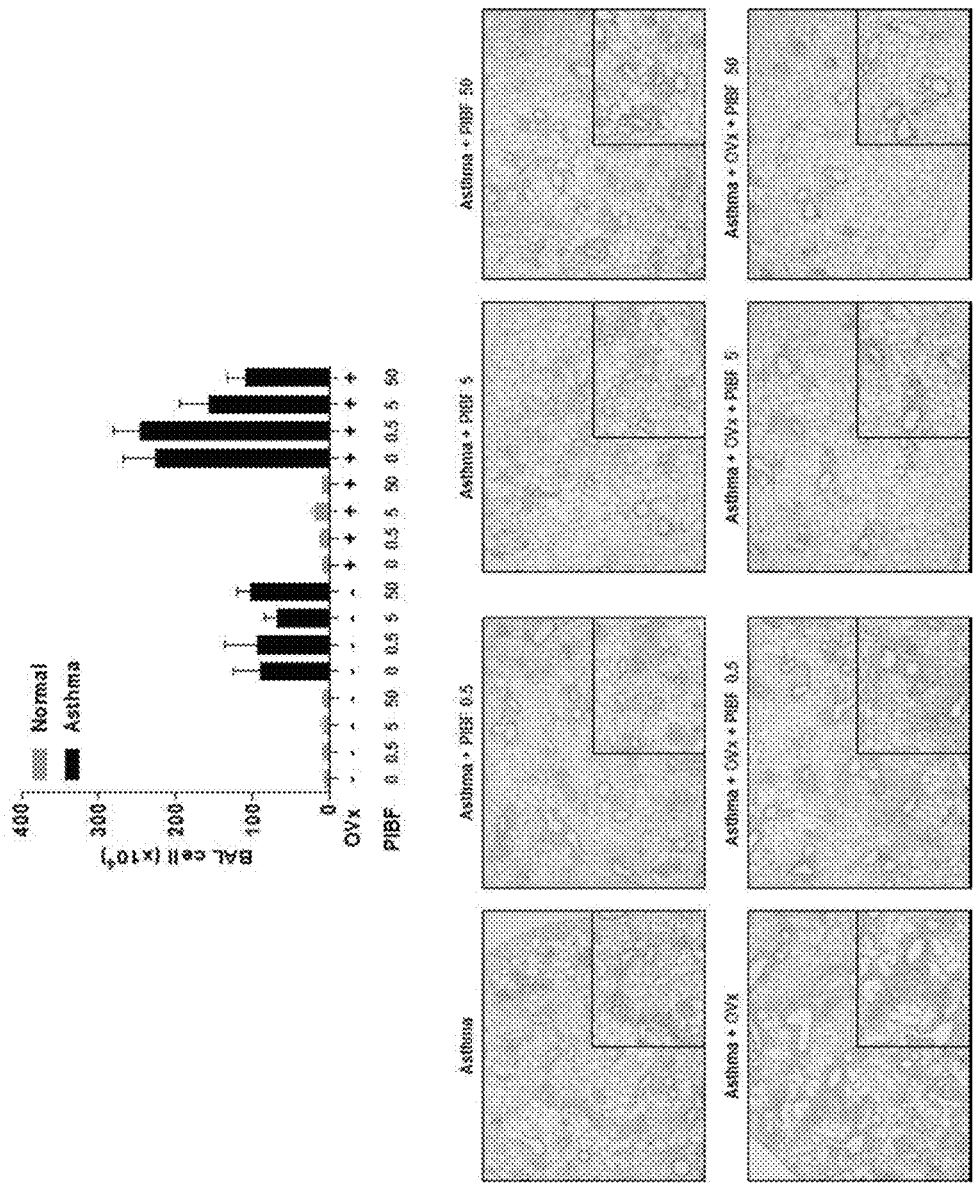
FIG. 7 shows the results of the influx of inflammatory cells into a bronchoalveolar lavage fluid and lung tissue through PIBF treatment.

2-3: Inflammatory Cell Influx Results in Bronchoalveolar Lavage Fluid and Lung Tissue Through PIBF Treatment From the results of analysis, it can be seen that airway inflammation worsened when asthma was induced in the mice in which menopause was induced, compared to the normal mice. In this case, it was confirmed that inflammation decreased in a dose-dependent manner when the mice were treated with PIBF. On the other hand, it was confirmed that no effect of decreasing inflammation was observed in an animal model in which asthma was induced in the normal mice, and tissue findings also reflected the same pattern (FIG. 7).

MODE FOR INVENTION

Preparation Examples

Preparation Example 1: Preparation of Pharmaceutical Formulation 1-1. Preparation of Powder

| | |
|---|---|
| PIBF protein of the present invention | 0.1 g |
| Lactose | 1.5 g |
| Talc | 0.5 g |

The above-described components were mixed, and filled in an airtight bag to prepare a powder.

1-2. Preparation of Tablet

| | |
|---|---|
| PIBF protein of the present invention | 0.1 g |
| Lactose | 7.9 g |
| Crystalline cellulose | 1.5 g |

The above-described components were mixed, and then subjected to a direct tableting method to prepare a tablet.

1-3. Preparation of Capsule

| | |
|---|---|
| PIBF protein of the present invention | 0.1 g |
| Corn starch | 5 g |
| Carboxy cellulose | 4.9 g |

The above-described components were mixed to prepare a powder, and the powder was then filled in a hard capsule according to a conventional method of preparing a capsule to prepare a capsule.

Preparation Example 2: Preparation of Health Foods 2-1. Preparation of Flour-Based Food 0.5 to 5.0 parts by weight of the PIBF protein of the present invention was added to wheat flour, and mixed. Then, the resulting mixture was used to prepare bread, cakes, cookies, crackers, and noodles.

2-2. Preparation of Dairy Products 5 to 10 parts by weight of the PIBF protein of the present invention was added to milk, and the resulting milk was used to prepare various dairy products such as butter and ice cream.

The invention claimed is:

1. A method of treating an asthma in post-menopausal women, comprising:
   administering or dosing a composition comprising a progesterone-induced blocking factor (PIBF) protein as an active ingredient to a subject.

2. The method of claim 1, wherein the PIBF protein has a molecular weight of 25 to 45 kDa.

3. The method of claim 1, wherein the composition further comprises one or more drugs selected from the group consisting of an anti-inflammatory agent, a bronchodilator, an anti-histamine, a decongestant, and an anti-tussive.

4. The method of claim 1, wherein the composition is formulated into the form of an oral formulation, a preparation for external use, a suppository, or a sterile injectable solution.

* * * * *

SEQUENCE LISTING

<160> NUMBER OF SEQ ID NOS: 7

<210> SEQ ID NO 1
<211> LENGTH: 1648
<212> TYPE: DNA
<213> ORGANISM: Artificial Sequence
<220> FEATURE:
<223> OTHER INFORMATION: recombinant PIBF

<400> SEQUENCE: 1

| | | | | | |
|---|---|---|---|---|---|
| ggccacagcg | gccgatgtcc | actcgatgtc | tcgaaaaatt | tcaaaggagt | caaaaaaagt | 60 |
| gaacatctct | agttctctgg | aatctgaaga | tattagttta | gaaacaacag | ttcctacgga | 120 |
| tgatatttcc | tcatcagaag | agcgagaggg | caaagtcaga | atcaccaggc | agctaattga | 180 |
| acgaaaagaa | ctacttcata | atattcagtt | actaaaaatt | gagctatccc | agaaaactat | 240 |
| gatgatcgac | aatttgaaag | tggattatct | tacaaagatt | gaagaattgg | aggagaaact | 300 |
| taatgatgca | cttcaccaga | agcagctact | aacattgaga | ttagcaaacc | aattggcttt | 360 |
| tcaacagaaa | gatgccagca | aatatcaaga | attaatgaaa | caagaaatgg | aaaccatttt | 420 |
| gttgagacag | aaacaactag | aagagacaaa | tcttcagcta | agaaaaaag | ctggagatgt | 480 |
| tcgtcgaaac | ctgcgtgact | ttgagttgac | agaagagcaa | tatattaaat | aaaaagcttt | 540 |
| tcctgaagat | cagcttttcta | ttcctgaata | tgtatctgtt | cgcttctatg | agctagtgaa | 600 |
| tccattaaga | aaggaaatct | gtgaactaca | agtgaaaaag | aatatcctag | cagaagaatt | 660 |
| aagtacaaac | aaaaaccaac | tgaagcagct | gacagaggaa | ttggcagcaa | tgaaacagat | 720 |
| tctcgttaag | atgcatagta | acattctga | aacagctta | cttctcacta | aacagaacc | 780 |
| aaaacatgtg | acagaaaatc | agaaatcaaa | gactttgaat | gtgcctaaag | agcatgaaga | 840 |
| caatatattt | acacctaaac | caacactctt | tactaaaaaa | gaagcacctg | agtggtctaa | 900 |
| gaaacaaaag | atgaagacct | tggccgcgtc | ggccgctagc | gagcccaaat | cttgtgacaa | 960 |
| aactcacaca | tgcccaccgt | gcccagcacc | tgaactcctg | ggggaccgt | cagtcttcct | 1020 |
| cttcccccca | aaacccaagg | acaccctcat | gatctcccgg | acccctgagg | tcacatgcgt | 1080 |
| ggtggtggac | gtgagccacg | aagaccctga | ggtcaagttc | aactggtacg | tggacggcgt | 1140 |
| ggaggtgcat | aatgccaaga | caaagccgcg | ggaggagcag | tacaacagca | cgtaccgtgt | 1200 |
| ggtcagcgtc | ctcaccgtcc | tgcaccagga | ctggctgaat | ggcaaggagt | acaagtgcaa | 1260 |
| ggtctccaac | aaagccctcc | cagccccat | cgagaaaacc | atctccaaag | ccaaagggca | 1320 |
| gccccgagaa | ccacaggtgt | acaccctgcc | cccatcccgg | gatgagctga | ccaagaacca | 1380 |
| ggtcagcctg | acctgcctgg | tcaaaggctt | ctatcccagc | gacatcgccg | tggagtggga | 1440 |
| gagcaatggg | cagccggaga | acaactacaa | gaccacgcct | cccgtgctgg | actccgacgg | 1500 |
| ctccttcttc | ctctacagca | agctcaccgt | ggacaagagc | aggtggcagc | aggggaacgt | 1560 |
| cttctcatgc | tccgtgatgc | atgaggctct | gcacaaccac | tacacgcaga | agagcctctc | 1620 |
| cctgtctccg | ggtaaatgat | agctcgag | | | | 1648 |

<210> SEQ ID NO 2
<211> LENGTH: 1648
<212> TYPE: DNA
<213> ORGANISM: Artificial Sequence
<220> FEATURE:
<223> OTHER INFORMATION: recombinant PIBF
<220> FEATURE:
<221> NAME/KEY: CDS
<222> LOCATION: (26)..(1636)

<400> SEQUENCE: 2

```
ggccacagcg gccgatgtcc actcg atg tct cga aaa att tca aag gag tca         52
                           Met Ser Arg Lys Ile Ser Lys Glu Ser
                             1               5 aaa aaa gtg aac atc tct agt tct ctg gaa tct gaa gat att agt tta        100
Lys Lys Val Asn Ile Ser Ser Ser Leu Glu Ser Glu Asp Ile Ser Leu
 10              15                  20                  25 gaa aca aca gtt cct acg gat gat att tcc tca tca gaa gag cga gag        148
Glu Thr Thr Val Pro Thr Asp Asp Ile Ser Ser Ser Glu Glu Arg Glu
                 30                  35                  40 ggc aaa gtc aga atc acc agg cag cta att gaa cga aaa gaa cta ctt        196
Gly Lys Val Arg Ile Thr Arg Gln Leu Ile Glu Arg Lys Glu Leu Leu
             45                  50                  55 cat aat att cag tta cta aaa att gag cta tcc cag aaa act atg atg        244
His Asn Ile Gln Leu Leu Lys Ile Glu Leu Ser Gln Lys Thr Met Met
         60                  65                  70 atc gac aat ttg aaa gtg gat tat ctt aca aag att gaa gaa ttg gag        292
Ile Asp Asn Leu Lys Val Asp Tyr Leu Thr Lys Ile Glu Glu Leu Glu
 75              80                  85 gag aaa ctt aat gat gca ctt cac cag aag cag cta cta aca ttg aga        340
Glu Lys Leu Asn Asp Ala Leu His Gln Lys Gln Leu Leu Thr Leu Arg
 90              95                 100                 105 tta gac aac caa ttg gct ttt caa cag aaa gat gcc agc aaa tat caa        388
Leu Asp Asn Gln Leu Ala Phe Gln Gln Lys Asp Ala Ser Lys Tyr Gln
                110                 115                 120 gaa tta atg aaa caa gaa atg gaa acc att ttg ttg aga cag aaa caa        436
Glu Leu Met Lys Gln Glu Met Glu Thr Ile Leu Leu Arg Gln Lys Gln
            125                 130                 135 cta gaa gag aca aat ctt cag cta aga gaa aaa gct gga gat gtt cgt        484
Leu Glu Glu Thr Asn Leu Gln Leu Arg Glu Lys Ala Gly Asp Val Arg
        140                 145                 150 cga aac ctg cgt gac ttt gag ttg aca gaa gag caa tat att aaa tta        532
Arg Asn Leu Arg Asp Phe Glu Leu Thr Glu Glu Gln Tyr Ile Lys Leu
    155                 160                 165 aaa gct ttt cct gaa gat cag ctt tct att cct gaa tat gta tct gtt        580
Lys Ala Phe Pro Glu Asp Gln Leu Ser Ile Pro Glu Tyr Val Ser Val
170                 175                 180                 185 cgc ttc tat gag cta gtg aat cca tta aga aag gaa atc tgt gaa cta        628
Arg Phe Tyr Glu Leu Val Asn Pro Leu Arg Lys Glu Ile Cys Glu Leu
                190                 195                 200 caa gtg aaa aag aat atc cta gca gaa gaa tta agt aca aac aaa aac        676
Gln Val Lys Lys Asn Ile Leu Ala Glu Glu Leu Ser Thr Asn Lys Asn
            205                 210                 215 caa ctg aag cag ctg aca gag gaa ttg gca gca atg aaa cag att ctc        724
Gln Leu Lys Gln Leu Thr Glu Glu Leu Ala Ala Met Lys Gln Ile Leu
        220                 225                 230 gtt aag atg cat agt aaa cat tct gag aac agc tta ctt ctc act aaa        772
Val Lys Met His Ser Lys His Ser Glu Asn Ser Leu Leu Leu Thr Lys
    235                 240                 245 aca gaa cca aaa cat gtg aca gaa aat cag aaa tca aag act ttg aat        820
Thr Glu Pro Lys His Val Thr Glu Asn Gln Lys Ser Lys Thr Leu Asn
250                 255                 260                 265 gtg cct aaa gag cat gaa gac aat ata ttt aca cct aaa cca aca ctc        868
Val Pro Lys Glu His Glu Asp Asn Ile Phe Thr Pro Lys Pro Thr Leu
                270                 275                 280 ttt act aaa aaa gaa gca cct gag tgg tct aag aaa caa aag atg aag        916
Phe Thr Lys Lys Glu Ala Pro Glu Trp Ser Lys Lys Gln Lys Met Lys
            285                 290                 295
```

```
acc ttg gcc gcg tcg gcc gct agc gag ccc aaa tct tgt gac aaa act      964
Thr Leu Ala Ala Ser Ala Ala Ser Glu Pro Lys Ser Cys Asp Lys Thr
        300                 305                 310 cac aca tgc cca ccg tgc cca gca cct gaa ctc ctg ggg gga ccg tca     1012
His Thr Cys Pro Pro Cys Pro Ala Pro Glu Leu Leu Gly Gly Pro Ser
        315                 320                 325 gtc ttc ctc ttc ccc cca aaa ccc aag gac acc ctc atg atc tcc cgg     1060
Val Phe Leu Phe Pro Pro Lys Pro Lys Asp Thr Leu Met Ile Ser Arg
330                 335                 340                 345 acc cct gag gtc aca tgc gtg gtg gtg gac gtg agc cac gaa gac cct     1108
Thr Pro Glu Val Thr Cys Val Val Val Asp Val Ser His Glu Asp Pro
                350                 355                 360 gag gtc aag ttc aac tgg tac gtg gac ggc gtg gag gtg cat aat gcc     1156
Glu Val Lys Phe Asn Trp Tyr Val Asp Gly Val Glu Val His Asn Ala
            365                 370                 375 aag aca aag ccg cgg gag gag cag tac aac agc acg tac cgt gtg gtc     1204
Lys Thr Lys Pro Arg Glu Glu Gln Tyr Asn Ser Thr Tyr Arg Val Val
        380                 385                 390 agc gtc ctc acc gtc ctg cac cag gac tgg ctg aat ggc aag gag tac     1252
Ser Val Leu Thr Val Leu His Gln Asp Trp Leu Asn Gly Lys Glu Tyr
        395                 400                 405 aag tgc aag gtc tcc aac aaa gcc ctc cca gcc ccc atc gag aaa acc     1300
Lys Cys Lys Val Ser Asn Lys Ala Leu Pro Ala Pro Ile Glu Lys Thr
410                 415                 420                 425 atc tcc aaa gcc aaa ggg cag ccc cga gaa cca cag gtg tac acc ctg     1348
Ile Ser Lys Ala Lys Gly Gln Pro Arg Glu Pro Gln Val Tyr Thr Leu
                430                 435                 440 ccc cca tcc cgg gat gag ctg acc aag aac cag gtc agc ctg acc tgc     1396
Pro Pro Ser Arg Asp Glu Leu Thr Lys Asn Gln Val Ser Leu Thr Cys
            445                 450                 455 ctg gtc aaa ggc ttc tat ccc agc gac atc gcc gtg gag tgg gag agc     1444
Leu Val Lys Gly Phe Tyr Pro Ser Asp Ile Ala Val Glu Trp Glu Ser
        460                 465                 470 aat ggg cag ccg gag aac aac tac aag acc acg cct ccc gtg ctg gac     1492
Asn Gly Gln Pro Glu Asn Asn Tyr Lys Thr Thr Pro Pro Val Leu Asp
        475                 480                 485 tcc gac ggc tcc ttc ttc ctc tac agc aag ctc acc gtg gac aag agc     1540
Ser Asp Gly Ser Phe Phe Leu Tyr Ser Lys Leu Thr Val Asp Lys Ser
490                 495                 500                 505 agg tgg cag cag ggg aac gtc ttc tca tgc tcc gtg atg cat gag gct     1588
Arg Trp Gln Gln Gly Asn Val Phe Ser Cys Ser Val Met His Glu Ala
                510                 515                 520 ctg cac aac cac tac acg cag aag agc ctc tcc ctg tct ccg ggt aaa     1636
Leu His Asn His Tyr Thr Gln Lys Ser Leu Ser Leu Ser Pro Gly Lys
            525                 530                 535 tgatagctcg ag                                                        1648

<210> SEQ ID NO 3
<211> LENGTH: 537
<212> TYPE: PRT
<213> ORGANISM: Homo sapiens
<220> FEATURE:
<223> OTHER INFORMATION: Full-length PIBF1

<400> SEQUENCE: 3

Met Ser Arg Lys Ile Ser Lys Glu Ser Lys Lys Val Asn Ile Ser Ser
1               5                   10                  15

Ser Leu Glu Ser Glu Asp Ile Ser Leu Glu Thr Thr Val Pro Thr Asp
            20                  25                  30
```

```
Asp Ile Ser Ser Ser Glu Glu Arg Glu Gly Lys Val Arg Ile Thr Arg
         35                  40                  45

Gln Leu Ile Glu Arg Lys Glu Leu Leu His Asn Ile Gln Leu Leu Lys
 50                  55                  60

Ile Glu Leu Ser Gln Lys Thr Met Met Ile Asp Asn Leu Lys Val Asp
 65                  70                  75                  80

Tyr Leu Thr Lys Ile Glu Leu Glu Glu Lys Leu Asn Asp Ala Leu
                 85                  90                  95

His Gln Lys Gln Leu Leu Thr Leu Arg Leu Asp Asn Gln Leu Ala Phe
                100                 105                 110

Gln Gln Lys Asp Ala Ser Lys Tyr Gln Glu Leu Met Lys Gln Glu Met
             115                 120                 125

Glu Thr Ile Leu Leu Arg Gln Lys Gln Leu Glu Glu Thr Asn Leu Gln
130                 135                 140

Leu Arg Glu Lys Ala Gly Asp Val Arg Arg Asn Leu Arg Asp Phe Glu
145                 150                 155                 160

Leu Thr Glu Glu Gln Tyr Ile Lys Leu Lys Ala Phe Pro Glu Asp Gln
                165                 170                 175

Leu Ser Ile Pro Glu Tyr Val Ser Val Arg Phe Tyr Glu Leu Val Asn
             180                 185                 190

Pro Leu Arg Lys Glu Ile Cys Glu Leu Gln Val Lys Lys Asn Ile Leu
             195                 200                 205

Ala Glu Glu Leu Ser Thr Asn Lys Asn Gln Leu Lys Gln Leu Thr Glu
         210                 215                 220

Glu Leu Ala Ala Met Lys Gln Ile Leu Val Lys Met His Ser Lys His
225                 230                 235                 240

Ser Glu Asn Ser Leu Leu Thr Lys Thr Glu Pro Lys His Val Thr
                245                 250                 255

Glu Asn Gln Lys Ser Lys Thr Leu Asn Val Pro Lys Glu His Glu Asp
             260                 265                 270

Asn Ile Phe Thr Pro Lys Pro Thr Leu Phe Thr Lys Lys Glu Ala Pro
             275                 280                 285

Glu Trp Ser Lys Lys Gln Lys Met Lys Thr Leu Ala Ala Ser Ala Ala
         290                 295                 300

Ser Glu Pro Lys Ser Cys Asp Lys Thr His Thr Cys Pro Pro Cys Pro
305                 310                 315                 320

Ala Pro Glu Leu Leu Gly Gly Pro Ser Val Phe Leu Phe Pro Pro Lys
                325                 330                 335

Pro Lys Asp Thr Leu Met Ile Ser Arg Thr Pro Glu Val Thr Cys Val
             340                 345                 350

Val Val Asp Val Ser His Glu Asp Pro Glu Val Lys Phe Asn Trp Tyr
             355                 360                 365

Val Asp Gly Val Glu Val His Asn Ala Lys Thr Lys Pro Arg Glu Glu
             370                 375                 380

Gln Tyr Asn Ser Thr Tyr Arg Val Val Ser Val Leu Thr Val Leu His
385                 390                 395                 400

Gln Asp Trp Leu Asn Gly Lys Glu Tyr Lys Cys Lys Val Ser Asn Lys
                405                 410                 415

Ala Leu Pro Ala Pro Ile Glu Lys Thr Ile Ser Lys Ala Lys Gly Gln
             420                 425                 430

Pro Arg Glu Pro Gln Val Tyr Thr Leu Pro Pro Ser Arg Asp Glu Leu
             435                 440                 445
```

```
Thr Lys Asn Gln Val Ser Leu Thr Cys Leu Val Lys Gly Phe Tyr Pro
        450                 455                 460

Ser Asp Ile Ala Val Glu Trp Glu Ser Asn Gly Gln Pro Glu Asn Asn
465                 470                 475                 480

Tyr Lys Thr Thr Pro Pro Val Leu Asp Ser Asp Gly Ser Phe Phe Leu
                485                 490                 495

Tyr Ser Lys Leu Thr Val Asp Lys Ser Arg Trp Gln Gln Gly Asn Val
        500                 505                 510

Phe Ser Cys Ser Val Met His Glu Ala Leu His Asn His Tyr Thr Gln
            515                 520                 525

Lys Ser Leu Ser Leu Ser Pro Gly Lys
        530                 535

<210> SEQ ID NO 4
<211> LENGTH: 894
<212> TYPE: DNA
<213> ORGANISM: artificial
<220> FEATURE:
<223> OTHER INFORMATION: Polynucleotides encoding 35kDa PIBF1
<220> FEATURE:
<221> NAME/KEY: CDS
<222> LOCATION: (1)..(894)

<400> SEQUENCE: 4
```

| | | | | | | | | | | | | | | | | |
|---|---|---|---|---|---|---|---|---|---|---|---|---|---|---|---|---|
| atg | tct | cga | aaa | att | tca | aag | gag | tca | aaa | aaa | gtg | aac | atc | tct | agt | 48 |
| Met | Ser | Arg | Lys | Ile | Ser | Lys | Glu | Ser | Lys | Lys | Val | Asn | Ile | Ser | Ser | |
| 1 | | | | 5 | | | | | 10 | | | | | 15 | | |
| tct | ctg | gaa | tct | gaa | gat | att | agt | tta | gaa | aca | aca | gtt | cct | acg | gat | 96 |
| Ser | Leu | Glu | Ser | Glu | Asp | Ile | Ser | Leu | Glu | Thr | Thr | Val | Pro | Thr | Asp | |
| | | | 20 | | | | | 25 | | | | | 30 | | | |
| gat | att | tcc | tca | tca | gaa | gag | cga | gag | ggc | aaa | gtc | aga | atc | acc | agg | 144 |
| Asp | Ile | Ser | Ser | Ser | Glu | Glu | Arg | Glu | Gly | Lys | Val | Arg | Ile | Thr | Arg | |
| | | 35 | | | | | 40 | | | | | 45 | | | | |
| cag | cta | att | gaa | cga | aaa | gaa | cta | ctt | cat | aat | att | cag | tta | cta | aaa | 192 |
| Gln | Leu | Ile | Glu | Arg | Lys | Glu | Leu | Leu | His | Asn | Ile | Gln | Leu | Leu | Lys | |
| 50 | | | | | 55 | | | | | 60 | | | | | | |
| att | gag | cta | tcc | cag | aaa | act | atg | atg | atc | gac | aat | ttg | aaa | gtg | gat | 240 |
| Ile | Glu | Leu | Ser | Gln | Lys | Thr | Met | Met | Ile | Asp | Asn | Leu | Lys | Val | Asp | |
| 65 | | | | | 70 | | | | | 75 | | | | | 80 | |
| tat | ctt | aca | aag | att | gaa | gaa | ttg | gag | gag | aaa | ctt | aat | gat | gca | ctt | 288 |
| Tyr | Leu | Thr | Lys | Ile | Glu | Glu | Leu | Glu | Glu | Lys | Leu | Asn | Asp | Ala | Leu | |
| | | | | 85 | | | | | 90 | | | | | 95 | | |
| cac | cag | aag | cag | cta | cta | aca | ttg | aga | tta | gac | aac | caa | ttg | gct | ttt | 336 |
| His | Gln | Lys | Gln | Leu | Leu | Thr | Leu | Arg | Leu | Asp | Asn | Gln | Leu | Ala | Phe | |
| | | | 100 | | | | | 105 | | | | | 110 | | | |
| caa | cag | aaa | gat | gcc | agc | aaa | tat | caa | gaa | tta | atg | aaa | caa | gaa | atg | 384 |
| Gln | Gln | Lys | Asp | Ala | Ser | Lys | Tyr | Gln | Glu | Leu | Met | Lys | Gln | Glu | Met | |
| | | 115 | | | | | 120 | | | | | 125 | | | | |
| gaa | acc | att | ttg | ttg | aga | cag | aaa | caa | cta | gaa | gag | aca | aat | ctt | cag | 432 |
| Glu | Thr | Ile | Leu | Leu | Arg | Gln | Lys | Gln | Leu | Glu | Glu | Thr | Asn | Leu | Gln | |
| 130 | | | | | 135 | | | | | 140 | | | | | | |
| cta | aga | gaa | aaa | gct | gga | gat | gtt | cgt | cga | aac | ctg | cgt | gac | ttt | gag | 480 |
| Leu | Arg | Glu | Lys | Ala | Gly | Asp | Val | Arg | Arg | Asn | Leu | Arg | Asp | Phe | Glu | |
| 145 | | | | | 150 | | | | | 155 | | | | | 160 | |
| ttg | aca | gaa | gag | caa | tat | att | aaa | tta | aaa | gct | ttt | cct | gaa | gat | cag | 528 |
| Leu | Thr | Glu | Glu | Gln | Tyr | Ile | Lys | Leu | Lys | Ala | Phe | Pro | Glu | Asp | Gln | |
| | | | | 165 | | | | | 170 | | | | | 175 | | |
| ctt | tct | att | cct | gaa | tat | gta | tct | gtt | cgc | ttc | tat | gag | cta | gtg | aat | 576 |
| Leu | Ser | Ile | Pro | Glu | Tyr | Val | Ser | Val | Arg | Phe | Tyr | Glu | Leu | Val | Asn | |
| | | | 180 | | | | | 185 | | | | | 190 | | | |

```
cca tta aga aag gaa atc tgt gaa cta caa gtg aaa aag aat atc cta    624
Pro Leu Arg Lys Glu Ile Cys Glu Leu Gln Val Lys Lys Asn Ile Leu
        195                 200                 205 gca gaa gaa tta agt aca aac aaa aac caa ctg aag cag ctg aca gag    672
Ala Glu Glu Leu Ser Thr Asn Lys Asn Gln Leu Lys Gln Leu Thr Glu
210                 215                 220 gaa ttg gca gca atg aaa cag att ctc gtt aag atg cat agt aaa cat    720
Glu Leu Ala Ala Met Lys Gln Ile Leu Val Lys Met His Ser Lys His
225                 230                 235                 240 tct gag aac agc tta ctt ctc act aaa aca gaa cca aaa cat gtg aca    768
Ser Glu Asn Ser Leu Leu Leu Thr Lys Thr Glu Pro Lys His Val Thr
                245                 250                 255 gaa aat cag aaa tca aag act ttg aat gtg cct aaa gag cat gaa gac    816
Glu Asn Gln Lys Ser Lys Thr Leu Asn Val Pro Lys Glu His Glu Asp
            260                 265                 270 aat ata ttt aca cct aaa cca aca ctc ttt act aaa aaa gaa gca cct    864
Asn Ile Phe Thr Pro Lys Pro Thr Leu Phe Thr Lys Lys Glu Ala Pro
        275                 280                 285 gag tgg tct aag aaa caa aag atg aag acc                            894
Glu Trp Ser Lys Lys Gln Lys Met Lys Thr
290                 295

<210> SEQ ID NO 5
<211> LENGTH: 298
<212> TYPE: PRT
<213> ORGANISM: artificial
<220> FEATURE:
<223> OTHER INFORMATION: Synthetic Construct

<400> SEQUENCE: 5

Met Ser Arg Lys Ile Ser Lys Glu Ser Lys Lys Val Asn Ile Ser Ser
1               5                   10                  15

Ser Leu Glu Ser Glu Asp Ile Ser Leu Glu Thr Thr Val Pro Thr Asp
            20                  25                  30

Asp Ile Ser Ser Ser Glu Glu Arg Glu Gly Lys Val Arg Ile Thr Arg
        35                  40                  45

Gln Leu Ile Glu Arg Lys Glu Leu Leu His Asn Ile Gln Leu Leu Lys
    50                  55                  60

Ile Glu Leu Ser Gln Lys Thr Met Met Ile Asp Asn Leu Lys Val Asp
65                  70                  75                  80

Tyr Leu Thr Lys Ile Glu Glu Leu Glu Glu Lys Leu Asn Asp Ala Leu
                85                  90                  95

His Gln Lys Gln Leu Leu Thr Leu Arg Leu Asp Asn Gln Leu Ala Phe
            100                 105                 110

Gln Gln Lys Asp Ala Ser Lys Tyr Gln Glu Leu Met Lys Gln Glu Met
        115                 120                 125

Glu Thr Ile Leu Leu Arg Gln Lys Gln Leu Glu Glu Thr Asn Leu Gln
    130                 135                 140

Leu Arg Glu Lys Ala Gly Asp Val Arg Arg Asn Leu Arg Asp Phe Glu
145                 150                 155                 160

Leu Thr Glu Glu Gln Tyr Ile Lys Leu Lys Ala Phe Pro Glu Asp Gln
                165                 170                 175

Leu Ser Ile Pro Glu Tyr Val Ser Val Arg Phe Tyr Glu Leu Val Asn
            180                 185                 190

Pro Leu Arg Lys Glu Ile Cys Glu Leu Gln Val Lys Lys Asn Ile Leu
        195                 200                 205
```

-continued

```
Ala Glu Glu Leu Ser Thr Asn Lys Asn Gln Leu Lys Gln Leu Thr Glu
            210                 215                 220

Glu Leu Ala Ala Met Lys Gln Ile Leu Val Lys Met His Ser Lys His
225                 230                 235                 240

Ser Glu Asn Ser Leu Leu Leu Thr Lys Thr Glu Pro Lys His Val Thr
                245                 250                 255

Glu Asn Gln Lys Ser Lys Thr Leu Asn Val Pro Lys Glu His Glu Asp
            260                 265                 270

Asn Ile Phe Thr Pro Lys Pro Thr Leu Phe Thr Lys Lys Glu Ala Pro
        275                 280                 285

Glu Trp Ser Lys Lys Gln Lys Met Lys Thr
    290                 295

<210> SEQ ID NO 6
<211> LENGTH: 12
<212> TYPE: DNA
<213> ORGANISM: Artificial Sequence
<220> FEATURE:
<223> OTHER INFORMATION: sfiI restriction site

<400> SEQUENCE: 6
ggccacagcg gc                                                    12

<210> SEQ ID NO 7
<211> LENGTH: 15
<212> TYPE: DNA
<213> ORGANISM: Artificial Sequence
<220> FEATURE:
<223> OTHER INFORMATION: NheI restriction site

<400> SEQUENCE: 7
ttggccgcgt cggcc                                                 15
```